US006673779B2

(12) United States Patent
Jacobus et al.

(10) Patent No.: US 6,673,779 B2
(45) Date of Patent: *Jan. 6, 2004

(54) METHOD OF TREATING CILIARY DYSKINESIA WITH DINUCLEOSIDE POLYPHOSPHATE COMPOUNDS OR UTP ANALOGUES

(75) Inventors: Karla M. Jacobus, Cary, NC (US); Benjamin R. Yerxa, Raleigh, NC (US); William Pendergast, Durham, NC (US); Richard C. Boucher, Jr., Chapel Hill, NC (US); Janet L. Rideout, Raleigh, NC (US); David J. Drutz, Chapel Hill, NC (US); Michael K. James, Raleigh, NC (US); Monroe Jackson Stutts, Chapel Hill, NC (US); Cara Geary, Cincinnati, OH (US); Eduardo R. Lazarowski, Durham, NC (US)

(73) Assignees: Inspire Pharmaceuticals, Inc., Durham, NC (US); The University of North Carolina at Chapel Hill, Chapel Hill, NC (US)

(*) Notice: Subject to any disclaimer, the term of this patent is extended or adjusted under 35 U.S.C. 154(b) by 0 days.

This patent is subject to a terminal disclaimer.

(21) Appl. No.: 10/163,804

(22) Filed: Jun. 5, 2002

(65) Prior Publication Data

US 2003/0036527 A1 Feb. 20, 2003

Related U.S. Application Data (63) Continuation-in-part of application No. 10/007,451, filed on Nov. 6, 2001, and a continuation-in-part of application No. 09/101,840, filed on Jul. 17, 1998, now Pat. No. 6,420,347, said application No. 09/101,840, filed as application No. PCT/US97/05101 on Mar. 27, 1997, is a continuation of application No. 08/624,914, filed on Mar. 27, 1996, now abandoned, said application No. 10/007,451, is a continuation of application No. 09/101,395, filed as application No. PCT/US98/02702 on Feb. 6, 1998, now Pat. No. 6,348,589, which is a continuation-in-part of application No. 08/798,508, filed on Feb. 10, 1997, now Pat. No. 5,837,861, and application No. 08/797,472, filed on Feb. 6, 1997, now Pat. No. 5,900,407.

(51) Int. Cl.[7] .............................................. A61K 31/70
(52) U.S. Cl. .................................... 514/51; 536/26.21
(58) Field of Search .......................... 514/51; 536/26.21

(56) References Cited

U.S. PATENT DOCUMENTS

| 5,260,073 | A | * | 11/1993 | Phipps | 424/465 |
|---|---|---|---|---|---|
| 5,292,498 | A | * | 3/1994 | Boucher, Jr. | 424/45 |
| 5,420,116 | A | * | 5/1995 | Puchelle et al. | 514/47 |
| 5,635,160 | A | * | 6/1997 | Stutts et al. | 514/47 |
| 5,789,391 | A | * | 8/1998 | Jacobus et al. | 514/51 |
| 5,837,861 | A | * | 11/1998 | Pendergast et al. | 536/25.6 |
| 5,900,407 | A | * | 5/1999 | Yerxa et al. | 514/47 |
| 5,958,897 | A | * | 9/1999 | Jacobus et al. | 514/49 |
| 5,972,904 | A | * | 10/1999 | Jacobus et al. | 514/51 |
| 5,981,506 | A | * | 11/1999 | Jacobus et al. | 514/47 |
| 6,348,589 | B1 | * | 2/2002 | Pendergast et al. | 536/25.6 |
| 6,420,347 | B1 | * | 7/2002 | Jacobus et al. | 514/51 |
| 6,423,694 | B1 | * | 7/2002 | Drutz et al. | 514/51 |
| 2002/0082417 | A1 | * | 6/2002 | Pendergast et al. | 536/26.26 |

FOREIGN PATENT DOCUMENTS

| WO | WO 95/10287 | 4/1995 | A61K/31/70 |
|---|---|---|---|
| WO | WO 96/40059 | 12/1996 | A61K/9/12 |
| WO | WO 97/29756 | 8/1997 | A61K/31/70 |
| WO | 9735591 | * 10/1997 | |
| WO | WO 98/34942 | 8/1998 | C07H/21/00 |

OTHER PUBLICATIONS

Nuutinen, "Activation of the Impaired Nasal Mucociliary Transport in Children: Preliminary Report," *International Journal of Pediatric Otorhinolaryngology*, 10, 47–52 (1985).*

Vovsi et al., "Importance of Hydrodynamic Indices for Pathogenic Treatment of Penetrating Wounds of the Eye (Russian)," *Zdravookhr. Tadzh.(USSR)*, 21(3), 35–37 (1974); EMBASE Record No.: 75036639.*

Bunin et al., "Effects of Riboflavin Mononucleotide, ATP and Drotaverine on Electroretinogram Intraocular Pressure. Ocular Hemodynamics and Drotaverine (Experimental and Clinical Investigation)(Russian)," *Vestn. Oftal.(USSR)*, *1975*, Issue No. 1, 65–68; EMBASE Record No. 75207772.*

Conigrave et al., "Review: $Ca^{2+}$–Mobilizing Receptors for ATP and UTP," *Cell Calcium*, 17(2), 111–119 (Feb., 1995).*

Mikhailovs et al., "Treatment of Retinal Pigment Degeneration—Involves Using Sodium Triphosphate Solution to Prevent Harmful Side Effects," *SU 129786 A(Soviet Patent)*, published Mar. 23, 1987; WPI–Derwent Acc. No. 87–290829/198741; only Derwent abstract supplied.*

Parr et al., "Cloning and Expression of a Human $P_{2U}$ Nucleotide Receptor, a Target for Cystic Fibrosis Pharmacotherapy," *Proc. National Academy Sciences (USA)*, 91(8), 3275–3279 (Apr. 12, 1994).*

(List continued on next page.)

*Primary Examiner*—James O. Wilson
*Assistant Examiner*—L E Crane
(74) *Attorney, Agent, or Firm*—Albert P. Halluin; Viola T. Kung; Howrey, Simon, Arnold & White, LLP (57) ABSTRACT

The present invention is directed to a method of stimulating ciliary beat frequency to promote mucociliary or cough clearance of retained mucus secretions from the lungs, sinuses, upper airways, ears, eyes, genito-urinary tract, spermatozoa, ovaries, fallopian tubes, neutrophils, and macrophages of a patient. The method comprises administering uridine triphosphates, adenosine triphosphates, cytidine triphosphates, or dinucleoside tetraphosphates and the derivatives thereof to an affected body of a patient, to treat dysfunction of the mucociliary clearance system as a result of impaired ciliary movement in the patient.

15 Claims, 2 Drawing Sheets

OTHER PUBLICATIONS

O'Connor, "Recent Developments in the Classification and Functional Significance of Receptors for ATP and UTP, Evidence for Nucleotide Receptors," *Life Sciences, 50*(12), 1657–1664 (1992).*

Souquet et al., "Le Syndrome de Dyskinesie Ciliaire Primitive (French)," *Lyon Medical, 250*(14), 79–85 (Sep. 30, 1983).*

Leung et al., "cAMP—But Not $Ca^{2+}$–Regulated Cl- Conductance in the Oviduct Is Defective in Mouse Model of Cystic Fibrosis," *American J. of Physiology, 268*(*Cell Physiology, 37*), C708–C712 (1995).*

Bissada et al., "Uropharmacology: XII. Miscellaneous Drugs Affecting Lower Urinary Tract," *Urology, 14*(3), 309–316 (Sep., 1979).*

Newhouse, "Primary Ciliary Dyskinesia: What Has It Taught Us About Pulmonary Disease?" *European J. of Respiratory Disease*, 64(Suppl. 127), 151–156 (1983).*

Knudsen et al., "Neutrophil Function in Primary Cilia Dyskinesia," *European Journal of Respiratory Disease*, 64(Suppl. 128), 476–478 (1983); only pp. 476–477 supplied.††*

Ottonello et al., "Neutrophil Dysfunction and Increased Susceptibility to Infection," *European Journal of Clinical Investigation, 25*, 687–692 (1995).*

Brown et al., "Evidence that UTP and ATP Regulate Phospholipase C Through a Common Extracellular 5'–Nucleotide Receptor In Human Airway Epithelial Cells," *Molecular Pharmacology, 40*, 648–655 (1991).*

Drutz et al., "Uridine 5'–Triphosphate (UTP) Regulates Mucocilliary Clearance Via Purinergic Receptor Activity," (disclosed at the "Purines '96" meeting) *Drug Development Research, 37*(3), 185 (1996); see Abstract at bottom of col. 1.*

Knowles et al., "Activation by Extracellular Nucleotides of Chloride Secretion in the Airway Epithelia of Patients with Cystic Fibrosis," *New England Journal of Medicine, 325*, 533–538 (Aug. 22, 1991).*

Lazarowski et al., "Pharmacological Selectivity of the Cloned Human $P_{2U}$–Purinoceptor: Potent Activation by Diadenosine Tetraphosphate," *British Journal of Pharmacology, 116*, 1619–1627 (1995).*

Lethem et al., "Nucleotide Regulation of Goblet Cells in Human Airway Epithelial Explants: Normal Exocytosis in Cystic Fibrosis," *American Journal of Repiratory Cell Molecular Biology, 9*, 315–322 (1993).*

Mason et al., "Regulation of Transepithelial Ion Transport and Intracellular Calcium by Extracellular ATP in Human Normal and Cystic Fibrosis Airway Epithelium," *British Journal of Pharmacology, 103*, 1649–1656 (1991).*

Noone et al., "Effects on Cough Clearance by Aerosolized Uridine–5'–Triphosphate ± Amiloride in Patients with Primary Ciliary Dyskenesia," *American Journal of Respiratory Critical Care Medicine, 154*, A530 (May 14, 1996); see Abstract at the top of col. 1.*

Olivier et al., "Acute Safety and Effects on Mucocilliary Clearance of Aerosolized Uridine 5'–Triphosphate ± Amiloride in Normal Human Adults," *American J. of Respiratory Critical Care Medicine, 154*, 217–223 (1996).*

Berkow et al. (eds.), *The Merck Manual of Diagonosis and Therapy, 16th Edition*, Merck & Co., Rahway, NJ, May, 1992, only pp. 666–667 supplied.*

Thomas (ed), *Taber's Cyclopedic Medical Dictionary, 17th Edition*, F.A. Davis Co., Philadelphia, PA, 1993, only pp. 1802–1804 supplied.*

Beers et al. (eds.), *The Merck Manual of Diagonosis and Therapy, 17th Edition*, Merck & Co., Whitehouse Station, NJ, Jun., 1999, only pp. 584–589 supplied.*

Venes (ed), *Taber's Cyclopedic Medical Dictionary, 19th Edition*, F.A. Davis Co., Philadelphia, PA, 2001, only pp. 420–421 supplied.*

Boucher, R., et al., "Mechanisms and Therapeutic Actions of Uridine Triphosphate in the Lung," *Adenosine Adenine Nucleotides: From Molecular Biology to Integrative Physiology*, 525–32 (1995).

Schidlow, D., "Primary Ciliary Dyskinesia (the immotile cilia syndrome)," *Ann Allergy* 73(6):457–68 (Dec. 1994).

Valerius, N., et al., "Defective Neutrophil Motility in Patients with Primary Ciliary Dyskinesia," *Eur J Clin Invest* 13(6):489–94 (Dec. 1983).

Greenstone, M., et al., "Hydrocephalus and Primary Ciliary Dyskinesia," *Arc Dis Child* 59(5):481–2 (May 1984).

Sleigh, M., "Primary Ciliary Dyskinesia," *Lancet ii.* 2(8244):476 (Aug. 1981).

Afzelius, B., "A Human Syndrome Caused by Immotile Cilia," *Science* 193(4250):317–9 (Jul. 1976).

Ballenger, J., "Acquired Ultrastructural Alterations of Respiratory Cilia and Clinical Disease: A Review," *Ann Otol Thinol Laryngol* 97(3 Pt 1):253–8 (May–Jun. 1988).

Pedersen, M., "Ciliary Activity and Pollution," *Lung* 168 Suppl:368–76 (1990).

Afzelius, B., et al., "Lack of Dynein Arms in Immotile Human Spermatozoa," *J Cell Biol* 66(2):225–32 (Aug. 1975).

Forrest, J., et al., "Activation of Nasal Cilia in Immotile Cilia Syndrome," *Am Rev Respir Dis* 120(3):511–5 (Sep. 1979).

Lansley, A., et al., "Control of the Beat Cycle of Respiratory Tract Cilia by Ca2+ and cAMP," *Am J Physiol.* 263(2 Pt 1):L232–42 (Aug. 1992).

* cited by examiner

METHOD OF TREATING CILIARY DYSKINESIA WITH DINUCLEOSIDE POLYPHOSPHATE COMPOUNDS OR UTP ANALOGUES

This application is a continuation-in-parts of U.S. application Ser. No. 09/101,840, filed Jul. 17, 1998, and Ser. No. 10/007,451, filed Nov. 6, 2001. U.S. application Ser. No. 09/101,840 is the National Stage of International Application No. PCT/US97/05101, filed Mar. 27, 1997, published Oct. 2, 1997 under PCT Article 21(2) in English; which is a continuation of U.S. application Ser. No. 08/624,914, filed Mar. 27, 1996, now abandoned. U.S. application Ser. No. 10/007,451 is a continuation of U.S. application Ser. No. 09/101,395, filed Jul. 10, 1998, now U.S. Pat. No. 6,348,589 which was the National Stage of International Application No. PCT/US98/02702, filed Feb. 6, 1998, published Aug. 13, 1998 under PCT Article 21(2) in English; which is a continuation-in-part of priority of U.S. application Ser. No. 08/798,508, filed Feb. 10, 1997, now U.S. Pat. No. 5,837,861, and U.S. application Ser. No. 08/797,472, filed Feb. 6, 1997, now U.S. Pat. No. 5,900,407.

TECHNICAL FIELD

This invention relates to a method of stimulating ciliary beat frequency to promote mucociliary or cough clearance of retained mucus secretions from the lungs, sinuses, ears, upper airways of a patient by administering certain uridine, adenosine, or cytidine triphosphates.

BACKGROUND OF THE INVENTION

Mucociliary clearance is an important defense mechanism of the human airway and middle/inner ear tract. Coordinated beats of cilia in the nose, trachea, bronchi, and middle ear propel the mucous layer toward the pharynx, carrying along with it microorganisms and other particles captured in the mucus. Normal function of this system depends on the frequency and coordination of ciliary beating and the properties of mucus. There are three components of the mucociliary clearance system: (1) the mucin layer, which is formed by secretion of mucins by goblet cells, (2) cilia, which transport the overlying mucin layer by synchronous beating, and (3) the periciliary liquid layer, which surrounds the cilia and is less viscous than the mucin layer, allowing free movement of the cilia. The electrolyte and water concentration of the periciliary layer is regulated by the luminal epithelial cells. (R. Boucher, et al., *Adenosine and Adenine Nudeotides: From Molecular Biology to Integrative Physiology*, p. 525–32 entitled "Mechanisms and Therapeutic Actions of Uridine Triphosphates in the Lung" (L. Belardinelli, et al. ed., Alumwer Academic Publishers, Boston 1995)).

Primary ciliary dyskinesia (PCD) is a congenital disease characterized by ultrastructural defects and motility disturbances of cilia, resulting in either absent or abnormal ciliary movement. The most common clinical manifestations of PCD are chronic respiratory disease (e.g., sinusitis, rhinitis, and bronchiectasis) and otitis media. Because PCD patients have either absent or severely impaired mucociliary clearance (MCC), the only available mechanism to clear or move secretions is cough. Cough clearance may be measured in a manner similar to that previously described for MCC. PCD also impairs the propulsion of spermatozoa, resulting in male infertility. (D. Schidlow, *Ann Alergy* 73(b), 457–68 (1995)). PCD also results in the impairment of cell motility of certain immune system cells, including neutrophils and macrophages. (N. Valerius, *Eur J Clin Invest* 13, 489–94 (1983)). PCD may be responsible for a form of hydrocephalus caused by ciliary malfunction. (M. Greenstone, *Arch Dis Child* 59,481–82 (1984)). The incidence of PCD has been calculated to be one in 16,000 live births, and an estimated 50% of affected individuals also have situs inversus (dextrocardia). The triad of bronchiectasis, sinusitis, and situs inversus (dextrocardia) is referred to as Kartageneis syndrome. (M. Sleigh, *Lancet* ii, 476 (1981)). It has been hypothesized that Kartagener's syndrome is caused by a lack of embryonic ciliary movement, resulting in the random rotation of the archenteron such that in half the cases there is situs inversus (dextrocardia) and in the other half there is normal cardia situs. (B. Afzelius, *Science* 193, 317–19 (1976)). The clinical course of PCD is characterized primarily by sinus and ear infections early in life with a progressive change to lung/lower airways diseases in adulthood. Chronic airways infections can lead to chronic obstructive changes in the pulmonary tissue, progressive loss of pulmonary function, and eventually death.

A secondary and more common form of ciliary dyskinesia is the acquired form of the disease. Chronic inflammation caused by severe viral or bacterial respiratory infections, chronic smoking, severe air pollution, chemical or thermal bums to the airways, intubation and mechanical ventilation, and near-drowning can result in changes in ciliary structure including disruption of the cellular membrane, loss or incorporation of microtubules, and formation of compound cilia, all of which can result in abnormal or absent ciliary function. (J. Ballenger *Ann Otol Rhinol Laryngol* 97 (3 Pt. 1), 253–58 (1988); U Pedersen *Lung* 168 Suppl., 368–76 (1990)). Respiratory infections which often lead to secondary ciliary dyskinesia include influenza, adult respiratory distress syndrome, and ventilator-associated pneumonia (VAP) in intensive care unit (ICU) patients. In some cases acquired ciliary dyskinesia may be reversed with appropriate and timely intervention; however, permanent damage and/or sustained exposure to the above factors may render the ciliary damage irreversible. The clinical manifestations and course would likely appear similar to PCD with respect to chronic lung infections, progressive loss of pulmonary function, and obstructive pulmonary disease.

The typical mammalian respiratory epithelial ceil contains about 200 cilia. Each cilium has nine peripheral microtubular doublets and two central tubules. Each peripheral doublet contains an A subunit and a B subunit, and each A subunit has a set of curved arms attached to it called the inner and outer dynein arms. These dynein arms contain ATPase-an enzyme which breaks down adenosine triphosphate (ATP), providing the energy for ciliary movement. Because the most common ultrastructural abnormality associated with primary ciliary dyskinesia is the total absence of dynein arms (B. Afzelius, et al, *J Cell Biol* 66, 225–32 (1975)), researchers began investigating whether extracellular application of ATP and ATPase could activate immotile cilia in vitro. (J. Forrest, et al.,*Am Rev Resp Dis* 120, 511–15 (1979)). Although the results appeared positive, the findings have not been consistently reproduced by others. It was later discovered that extracellular application of $Ca^{2+}$ and cAMP could increase the beat frequency of respiratory tract cilia. (A. Lansley, et al., *Am J. Physiol* 263, L232–42) (1992)). It has not been definitively established that any therapy will stimulate cilia beat in cases where complete ciliary immotility has been demonstrated. In such cases, it might be of therapeutic benefit to increase hydration of the viscous mucous secretions.

It is known that ATP/UTP stimulates ciliary beat frequency in nasal epithelial cells (R. Boucher, et al., supra);

UTP stimulates mucin secretion by goblet cells (M. Lethem, et al., *Am J Respir Cel Mol Biol* 9, 315–22 (1993)); and UTP stimulates Cl secretion in airway epithelial cells, which increases hydration of the periciliary liquid layer (M. Knowles, et al., *N Eng J. Med* 325, 533–38 (1991)).

SUMMARY OF THE INVENTION

This invention is directed to a method of stimulating ciliary beat frequency in a subject in need of such treatment. The method comprises administering to a patient a compound of Formula I, II, III, or IV, or a pharmaceutically acceptable salt thereof, in an amount effective to stimulate ciliary beat frequency, for example, in the lung, middle/inner ear, eyes, sinuses, upper airway, genito-urinary tract; spermatozoa cells, or certain cells of the immune system, including neutrophils and macrophages.

Formula I wherein:

$X_1$, $X_2$, and $X_3$ are each independently selected from the group consisting of OH and SH;

$R_1$ is selected from the group consisting of O, imido, methylene, and dihalomethylene; and $R_2$ is selected from the group consisting of H and Br;

Formula II wherein:

$R_1$, $X_1$, $X_2$, and $X_3$ are defined as in Formula I, $R_3$, and $R_4$ are H while $R_2$ is nothing and there is a double bond between the N-1 and C-6 (adenine), or $R_3$ and $R_4$ are H while $R_2$ is O and there is a double bond between N-1 and C-6 (adenine 1-oxide);

$R_4$ is nothing while $R_3$ and $R_2$ taken together are —CH=CH—, forming a ring from N-6 to N-1 with a double bond between N-6 and C-6 (1, $N^6$-etheno-9-adenine);

Formula III wherein:

$R_1$, $X_1$, $X_2$, and $X_3$ are defined as in Formula I, $R_5$ and $R_6$ are H while $R_7$ is nothing and there is a double bond between N-3 and C-4 (cytosine), or $R_5$ is nothing while $R_6$ and $R_7$ taken together are —CH=CH—, forming a ring from N-3 to N-4 with a double bond between N-4 and C-4 (3, $N^4$-ethenocytosine);

Formula IV wherein:

X is oxygen, methylene, difluoromethylene, imido;

n=0, 1 or 2;

m=0, 1 or 2;

n+m=0, 1, 2, 3 or 4;

Z=OH or $N_3$;

Z'=OH or $N_3$;

Y=H or OH;

Y'=H or OH;

B and B' are each independently a purine residue (as in Formula IVa) or a pyrimidine residue (as in Formula IVb) linked through the 9- or 1-position, respectively.

The compounds of the present invention are highly selective agonists of the $P2Y_2$ and/or $P2Y_4$ purinergic receptor; thus, they are useful in the treatment of chronic obstructive pulmonary diseases such as chronic bronchitis, PCD, and cystic fibrosis, and useful in the treatment of immobilized patients who are at risk for developing pneumonia. Furthermore, because of their general ability to clear retained mucus secretions and stimulate ciliary beat frequency, the compounds of the present invention are useful in the treatment of sinusitis, otitis media and nasolacrimal duct obstruction. They are also useful for the treatment of dry eye, retinal detachment, wound healing, upper respiratory infection, and chronic inflammation caused by viral or bacterial infection. In addition, because of the pharmacological actions of these compounds, they are useful in facilitating sputum induction procedures. Additionally, the compounds of the present inventions could enhance the performance of athletes by increasing the clearance of mucous secretions from the lungs.

DESCRIPTION OF THE SPECIFIC EMBODIMENTS

The present invention is directed to a method of stimulating ciliary beat frequency in a subject in need of such treatment. The present invention is also directed to a method of treating ciliary dyskinesia. The method comprises the steps of administering to the subject a compound of Formula I, II, III or IV, or pharmaceutically acceptable salt thereof, in a pharmaceutical carrier having an amount of said compound effective to increase ciliary beat frequency in the affected part of the body.

The method of the present invention can be used to stimulate ciliary beat frequency in a subject in need of such treatment for any reason, including (but not limited to) increasing the mucociliary clearance of retained secretions in the lungs, sinuses, upper airway, or middle and inner ears. The method of the present invention can also be used to treat primary ciliary dyskinesia, secondary ciliary dyskinesia, Kartageneis syndrome, otitis media, cystic fibrosis, upper respiratory infection, chronic inflammation caused by viral or bacterial infection, diseases involving the dysfunction of the ocular or genito-urinary mucociliary clearance defense system caused by impairment of ciliary movement, diseases of the immune system caused by impairment of ciliary movement of neutrophils and macrophages, hydrocephalus caused by impairment of ciliary movement, male infertility caused by impairment of the ciliary propulsion of the spermatozoa, female infertility caused by impairment of ciliary movement on the luminal epithelial cells of the ovaries or fallopian tubes, or any other disease caused by an impairment of ciliary movement.

The present invention increases mucociliary clearance in three ways: (1) by increasing the ciliary beat frequency of cilia on the surface of luminal epithelia cells, (2) by increasing the secretions of mucins by goblet cells, and (3) by increasing the secretion of water into the periciliary liquid layer by luminal epithelial cells. The mucins secreted by goblet cells form a layer on top of the cilia and captures foreign particles, including viruses and bacteria; the mucin layer is transported by the wave-like action of cilia, and the movement of cilia is facilitated by the composition and hydration of the periciliary liquid layer surrounding the cilia. Although the primary aspect of the present invention is to increase ciliary beat frequency in patients afflicted with ciliary dyskinesia, in patients whose cilia are permanently incapable of any movement regardless of treatment, the active compounds of the present invention also facilitate the clearance of retained mucous secretions by increasing the secretion of water into the periciliary liquid layer and by increasing the secretion of mucins by goblet cells.

Additionally, because of the well-demonstrated ability of the active compounds of the present invention to enhance lung clearance in normal subjects, the active compounds of the present invention can accelerate the clearance of any type of inhaled foreign materials from the airways. This would prove beneficial in a number of situations-biological warfare, e.g. the chemical warfare agent ricin; smoke inhalation; industrial exposure to inhaled toxins (resulting in e.g., silicosis, anthracosis, and the gamut of so-called pneumoconioses); and allergic reaction to inhaled particles such as pollen.

Furthermore, the ability of the active compounds of the present invention to increase lung clearance would also prove beneficial in the diagnosis of lung disease; specifically, to improve the quality of radioisotopic scans of the lungs by removing the secretions that might otherwise obscure the visualization of ventilated portions of the lung. In radioisotopic lung scanning, the mismatch of ventilated versus perfused lung is used to identify areas of pulmonary infarction. As a result of improved aeration of the lungs after administering the active compounds of the present invention, the ventilated portions of the scan would be more distinct, and the diagnostician would be in a better position to clearly identify true mismatches.

Applicant has discovered that extracellular triphosphate nucleotides, especially uridine S-triphosphate (UTP) modulates all three components of the mucociliary transport system: 1) Increasing ciliary beat frequency; 2) Stimulating mucin secretion by goblet cells; and 3) Stimulating Cl secretion, which increases hydration. Applicant has also demonstrated that UTP is safe and improves cough clearance in primary ciliary dyskinesia (PCD) patients (P. Noone, et al., abstract submitted to the 1996 International Conference of The American Thoracic Society, May 10–15, *Am. J. Respir. Crit. Care Med.* April, 1996, 153 A1-940).

In summary, applicant has discovered that a variety of clinical manifestations of ciliary dyskinesia, such as absent or impaired mucociliary clearance in the respiratory and middle/inner ear tract, impaired propulsion of spermatozoa, and impaired motility of neutrophils and macrophages can be improved or alleviated by administering UTP and its related compounds, as well as other nucleoside phosphates to the affected part of the body.

The present invention is concerned primarily with the treatment of human subjects, but may also be employed for the treatment of other mammalian subjects, such as dogs and cats, for veterinary purposes.

General structures of Formulae I, II, III and W are as follows:

Formula I wherein:

$X_1$, $X_2$, and $X_3$ are each independently selected from the group consisting of OH and SH;

$R_1$ is selected from the group consisting of O, imido, methylene, and dihalomethylene; and $R_2$ is selected from the group consisting of H and Br.

Particularly preferred compounds of Formula I are uridine 5'-triphosphate (UTP) and uridine 5'-O-(3-thiotriphosphate) (UTPγS).

Formula II wherein:

$R_1$, $X_1$, $X_2$, and $X_3$ are defined as in Formula I,

$R_3$, and $R_4$ are H while $R_2$ is nothing and there is a double bond between the N-1 and C-6 (adenine), or $R_3$ and $R_4$ are H while $R_2$ is 0 and there is a double bond between N-1 and C-6 (adenine 1-oxide);

$R_4$ is nothing while $R_3$ and $R_2$ taken together are —CH=CH—, forming a ring from N-6 to N-1 with a double bond between N-6 and C-6 (1, $N^6$-etheno-9-adenine);

Preferred compounds of Formula II are adenosine 5'-triphosphate (ATP) or 1,$N^6$-ethenoadenosine triphosphate and adenosine 1-oxide triphosphate.

Formula III wherein:

$R_1$, $X_1$, $X_2$, and $X_3$ are defined as in Formula I, $R_5$ and $R_6$ are H while $R_7$ is nothing and there is a double bond between N-3 and C-4 (cytosine), or $R_5$ is nothing while $R_6$ and $R_7$ taken together are —CH≡CH—, forming a ring from N-3 to N-4 with a double bond between N-4 and C-4 (3, $N^4$-ethenocytosine).

Formula IV wherein:

X is oxygen, methylene, difluoromethylene, imido;

n=0, or 2;

m=0, or 2;

n+m=0, 1, 2, 3 or 4;

Z=OH or $N_3$;

Z'=OH or $N_3$;

Y=H or OH;

Y'=H or OH;

B and B' are each independently a purine residue (as in Formula IVa) or a pyrimidine residue (as in Formula IVb) linked through the 9- or 1-position, respectively;

Formula IVa wherein:

R₁ is a hydrogen, or an alkyl or aryl moiety as defined below or ω-A(C$_{1-6}$alkyl)CONH(C$_{1-6}$alkyl) wherein A is amino, mercapto, hydroxy or carboxyl;

R₂ is O (adenine 1-oxide derivatives), or is absent (adenine derivatives); or

R₁ and R₂ taken together form a 5-membered fused imidazole ring (1, N⁶-ethenoadenine derivatives), optionally substituted on the 4- or 5-positions of the etheno moiety with alkyl, aryl or aralkyl moieties as defined below;

R₃ is alkyl, aryl or aralkyl, alkylamino, arylamino or aralkylamino (NHR'); alkoxy, aryloxy or aralkyloxy (OR'); alkylthio, arylthio or aralkylthio (SR') as defined below; or ω-A(C$_{1-6}$-alkyl)CONH(C$_{1-6}$alkyl)B- wherein A and B are independently amino, mercapto, hydroxy or carboxyl; or pharmaceutically acceptable esters, amides or salts thereof;

Formula IVb wherein:

R₄ is hydrogen, hydroxy, mercapto, amino, cyano, aralkoxy, C$_{1-6}$ alkylthio, C$_{1-6}$ alkoxy, C$_{1-6}$ alkylamino or dialkylamino, the alkyl groups optionally linked to form a heterocycle;

R₅ is hydrogen, acyl (e.g., acetyl or benzoyl), C$_{1-6}$ alkyl, aroyl, optionally functionalized as defined below, C$_{1-5}$ alkanoyl, benzoyl, or sulphonate;

R₆ is hydroxy, mercapto, alkoxy, aralkoxy, C$_{1-6}$alkylthio, amino, C$_{1-5}$ disubstituted amino, triazolyl, alkylamino or dialkylamino, where the alkyl groups are optionally linked to form a heterocycle or link to N³ to form an optionally substituted ring; or R₅ and R₆ taken together form a 5-membered fused imidazole ring between positions 3 and 4 of the pyrimidine ring (3,N⁴-ethenocytosine derivatives) optionally substituted on the 4- or 5-positions of the etheno moiety with alkyl, aryl or aralkyl moieties as defined below.

R₇ is hydrogen, hydroxy, cyano, nitro, alkenyl with the alkenyl moiety optionally linked through oxygen to form a ring optionally substituted on the carbon adjacent to the oxygen with alkyl or aryl groups, substituted alkynyl, halogen, substituted alkyl, perhalomethyl (e.g., CF₃), C$_{2-6}$ alkyl, C$_{2-3}$ alkenyl, or substituted ethenyl (e.g., allylamino, bromovinyl and ethyl propenoate, or propenoic acid), C$_{2-3}$ alkynyl or substituted alkynyl; or together R₆–R₇ may form a 5 or 6-membered saturated or unsaturated ring bonded through N or O at R₆, such a ring may contain substituents that themselves contain functionalities; provided that when R₈ is amino or substituted amino, R₇ is hydrogen; and R₈ is hydrogen, amino or substituted amino, alkoxy, arylalkoxy, alkylthio, arylalkylthio, carboxamidomethyl, carboxymethyl, methoxy, methylthio, phenoxy or phenylthio; or pharmaceutically acceptable esters, amides or salts thereof.

In the general structures of Formula IVa and IVb above, the acyl groups include alkanoyl or aroyl groups. The alkyl groups include straight or branched chain containing 1 to 8 carbon atoms, preferably 1 to 4 carbon atoms optionally substituted by one or more appropriate substituents, as described below. The aryl groups including the aryl moieties of such groups as aryloxy are preferably phenyl groups optionally substituted by one or more appropriate substituents, as described below. The above-mentioned alkenyl and alkynyl groups advantageously contain 2 to 8 carbon atoms, particularly 2 to 6 carbon atoms, e.g., ethenyl or ethynyl, optionally substituted by one or more appropriate substituents as described below.

Appropriate substituents on the above-mentioned alkyl, alkenyl, alkynyl, and aryl groups are advantageously selected from halogen, hydroxy, C$_{1-4}$ alkoxy, C$_{1-4}$ alkyl, C$_{6-10}$ aryl, C$_{7-12}$ arylalkyl, C$_{7-12}$ arylalkoxy, carboxy, cyano, nitro, sulfonamido, sulfonate, phosphate, sulfonic acid, amino and substituted amino wherein the amino is singly or doubly substituted by a C$_{1-4}$ alkyl, and when doubly substituted, the alkyl groups optionally being linked to form a heterocycle.

For simplicity, Formulae I–IV herein illustrate the active compounds in the naturally occurring D-configuration, but the present invention also encompasses compounds in the L-configuration, and mixtures of compounds in the D-and L-configurations, unless otherwise specified. The naturally occurring D-configuration is preferred.

Compounds illustrative of the compounds of Formula I above include: (a) uridine 5'-triphosphate (UTP); (b) uridine 5'-O-(3-thiotiphosphate) (UTPγS); and (c) 5-bromo-uridine 5'-triphosphate (5-BrUTP). These compounds are known or may be made in accordance with known procedures, or variations thereof which will be apparent to those skilled in the art. See generally N. Cusack and S. Hourani, *Annals N.Y. Acad. Sci.* 603, 172–81 (entitled "Biological Actions of Extracellular ATP"). For example, UTP may be made in the manner described in Kenner, et al., *J. Chem. Soc.* 1954, 2288; or Hall and Khorana, *J. Am. Chem. Soc.* 76, 5056 (1954). See Merck Index, Monograph No. 9795 (11th Ed. 1989). UTPγS may be made in the manner described in R S. Goody and F. Eckstein, *J. Am. Chem. Sot.* 93, 6252 (1971).

Compounds illustrative of the compounds of Formula II above include adenosine 5'-triphosphate (ATP) and 1, N⁶-ethenoadenosine triphosphate. Compounds illustrative of the compounds of Formula III above include cytidine 5'-triphosphate and 3, N⁴-ethenocytidine triphosphate. These compounds can be made in accordance with known procedures, or variations thereof which will be apparent to those skilled in the art. For example, phosphorylation of nucleosides by standard methods such as D. Hoard and D. Ott, *J. Am. Chem. Soc.* 87, 1785–1788 (1965); M. Yoshikawa, et al., *Tetrahedron Lett.* 5065–68 (1967) and idem., *Bull. Gem Soc.* (Jpn) 42, 3505–08 (1969); J. Moffatt and H. Khorana, *J. Am. Chem. Soc.* 83, 649–59 (1961); and B. Fischer, et al., *J. Med. Chem.* 36, 3937–46 (1993) and references therein. Etheno derivatives of cytidine and adenosine are prepared by known methods such as: N. Kotchetkov, et al., *Tetrahedron Lett.* 1993 (1971); J. Barrio, et al., *Biochem. Biophys. Res. Common,* 46, 597 (1972); J. Secrist, et al., *Biochemistry* 11, 3499 (1972); J. Bierndt, et al., *Nucleic Acids Res.* 5, 789 (1978); K. Koyasuga-Mikado, et al., *Chem. Pharm. Bull.* (Tokyo) 28, 932 (1980). Derivatives with alpha, beta and gamma thiophosphorus groups can be derived by the following or by adapting methods of: J. Ludwig and F. Eckstein, *J. Org Chem.* 54, 631–35 (1989); F. Eckstein and R. Goody, *Biochemistry,* 15, 1685 (1976); R. Goody and F. Eckstein, J. Am. Chem. Soc. 93, 6252 (1971).

Compounds of Formula I, II, or III, where $R_1$ is $CCl_2$ and $CF_2$, can be prepared by methods similar to that described in G. Blackbum, et al., *J. Chem. Sot. Perkin Trans.* I, 1119–25 (1984). Compounds of Formula I, II, or III, where $R_1$ is $CH_2$, can be prepared by methods similar to that described in T. Myers, et al., *J. Am. Chem Soc.* 85, 3292–95 (1963).

The substituted derivatives of adenine in Formula IVa include adenine 1-oxide; 1,$N^6$-(4- or 5-substituted etheno) adenine; 6-substituted adenine; or 8-substituted aminoadenine, where R' of wherein the 6- or 8-HNR' groups are chosen from among: arylalkyl ($C_{1-6}$) groups with the aryl moiety optionally functionalized as described below; alkyl; and alkyl groups with functional groups therein, such as: ([6-aminohexyl]carbamoylmethyl)-, and ω-acylated-amino (hydroxy, thiol and carboxy)alkyl($C_{2-10}$)- and their ω-acylated-amino (hydroxy, thiol and carboxy) derivatives where the acyl group is chosen from among, but not limited to, acetyl, trifluoroacetyl, benzoyl, substituted-benzoyl, etc; the carboxylic moiety is present as its ester or amide derivative, for example, the ethyl or methyl ester or its methyl, ethyl or benzamido derivative. The ω-amino (hydroxy, thiol) moiety is optionally alkylated with a $C_{1-4}$ alkyl group. Compounds illustrative of the compounds of Formula IV include ($P^1$, $P^4$-di(adenosine-5') tetraphosphate. ($A_2P_4$) or $P^1,P^4$-di(uridine-5'-) tetraphosphate ($U_2P_4$). These compounds can be made in accordance with known procedures, or variations thereof which will be described by: P. Zamecnik, et al. *Proc. Natl. Acad. Sci. USA* 89, 83842 (1981); and K. Ng and L. E. Orgel, *Nucleic Acids Res.* 15 (8), 3572–80 (1987).

In addition, UTP, ATP, CTP, $A_2P_{4,3}$,$N^4$-ethenocytidine triphosphate, 1, $N^6$-ethenoadenine triphosphate, adenosine 1-oxide triphosphate, ATPγS, ATPβS, ATPαS, AMPPCH$_2$P, AMPPNHP, $N^4$-ethenocytidine and 1, $N^6$-ethenoadenosine are commercially available, for example, from Sigma Chemical Company, St. Louis, Mo. 63178.

The active compounds of Formulae I–IV can be administered by themselves or in the form of their pharmaceutically acceptable salts, e.g., an alkali metal salt such as lithium, sodium or potassium, an alkaline earth metal salts such as manganese, magnesium and calcium or an ammonium and tetraalkyl ammonium salts, $NX_4^+$ (wherein X is $C_{1-4}$ alkyl group). Pharmaceutically acceptable salts are salts that retain the desired biological activity of the parent compound and do not impart undesired toxicological effects.

The active compounds disclosed herein are administered to the lungs, sinuses, upper airways, ears, eyes, spermatozoa, ovaries or fallopian tubes, or genitourinary tract by a variety of suitable means, but are preferably administered by administering a nebulized form of the active compound into their respiratory tract, such that the active compound enters the lungs and reaches the area of the body afflicted with impaired ciliary movement either directly or via systemic absorption and circulation. The active compound can be aerosolized in a variety of forms, such as, but not limited to, dry powder inhalants, metered dose inhalants, or liquid/liquid suspensions. In dry powder delivery, the UTP may be formulated alone or in combination with diluent or carrier, such as sugars (e.g., lactose, sucrose, trehalose, mannitol) where the compounds may be intimately incorporated in the matrix through glassification or simply admixed with the carrier, or other acceptable excipients for lung or airway delivery. The dry powder may be obtained by methods known in the art, such as spray drying, milling, freeze-drying, super-critical fluid manufacturing or via controlled crystallization or precipitation The dosage of active compound to stimulate ciliary beat frequency will vary depending on the condition being treated and the state of the subject, but generally an effective amount is the amount sufficient to achieve concentrations of active compound on the lungs, sinuses, upper airways, ears, eyes, or genito-urinary surfaces of the subject of from about $10^{-7}$ to about $10^{-1}$ Moles/liter, and more preferably from about $10^{-6}$ to about $10^{-1}$ Moles/liter.

Depending upon the solubility of the particular formulation of active compound administered, the daily dose to promote fluid drainage may be divided among one or several unit dose administrations. Preferably, the daily dose is no more than four times per day.

Another means of administering the active compound to the lungs, sinuses, upper airways, ears, eyes, or genito-urinary tract of the patient to promote fluid/secretion drainage include any oral form of the active compound, administered to the patient either by means of a liquid suspension of the active compound which is poured into the mouth of the patient, or by means of a pill form swallowed by the patient.

Another means of administering an effective amount of the active compound to the lungs, sinuses, upper airways, eyes, or middle and inner ears involve administering a liquid/liquid suspension (either a nasal spray of respirable particles which the subject inhales, or nasal drops of a liquid formulation, or eye drops of a liquid formulation) comprised of the active compound. Liquid pharmaceutical compositions of the active compound for producing a nasal spray or nasal or eye drops may be prepared by combining the active compound with a suitable vehicle, such as sterile pyrogen free water or sterile saline by techniques known to those skilled in the art.

Another means of administering the active compound to the middle ear or eye include any topical form of the active compound, administered as a cream or gel to the outer ear or eye, which would subsequently permeate through the tympanic membrane or cornea into the middle ear or lens of the patient.

Another means of administering the active compound to the middle ear, genito-urinary tract, or eye involve an injected form of the active compound, injected from the outer ear directly through the tympanic membrane into the middle ear, injected into the genito-urinary tract, or injected into the eye: This could involve a patch containing UTP which would be applied directly to the tympanic membrane.

Another means of administering the active compound to the lungs, sinuses, upper airways, middle and inner ears, eyes, or genito-urinary tract involve a suppository form of the active compound, such that a therapeutically effective amount of the compound reaches the lungs, sinuses, upper airways, middle ear, eye, genito-urinary tract, or male or female reproductive systems via systemic absorption.

Another means of administering the active compound involve intra-operative instillation of a gel, cream, or liquid suspension form of the active compound such that a therapeutically effective amount reaches the lungs, sinuses, upper airways, middle and inner ears, eyes, or genito-urinary tract.

An additional means of administering the active compound involve ex vivo administration of the active compound to the spermatozoa by means of a topical, injection, or immersion form of the compound, such that a therapeutically effective amount of said compound contacts the spermatozoa having impaired ciliary movement.

An additional means of administering the active compound involve administration of the active compound via a transdermal patch, in which the active compound would be delivered to the affected are via local absorption or systemic absorption and circulation.

Compounds according to Formulae I–IV also have therapeutic benefit when used in combination with other agents used to treat ciliary dyskinesia, such as, but not limited to: antibiotics; vaccines; decongestants, mucolytic agents; non-steroidal antiinflammatory agents; steroids; antiviral agents; and bronchodilators. Compounds of Formulae I–IV may also be used in combination with other treatments under development, such as gene therapy. Compound of Formulae I–IV can also be used in combination with the recently discovered therapeutic protein defensin.

A second aspect of the present invention is a pharmaceutical formulation containing the compound of Formula I, II, III, or IV in an amount effective to stimulate ciliary beat frequency in: the epithelial cells of the lungs or middle and inner ears; the mucous clearance defense system of the eyes or genito-urinary tract; spermatozoa cells; the ovaries or fallopian tubes; or certain cells of the immune system, including neutrophils and macrophages, in a pharmaceutically acceptable carrier.

A third aspect of the present invention is the use of the active compounds disclosed herein for the manufacture of a medicament for the therapeutic stimulation of ciliary beat frequency in: the epithelial cells of the lungs, the upper airways or middle and inner ears; the mucous clearance defense system of the eyes or genito-urinary tract; spermatozoa cells; the ovaries or fallopian tubes; or certain cells of the immune system, including neutrophils and macrophages, of a patient in need of such treatment.

The present invention is explained in the Examples which follow. These examples are intended as illustrative of the invention, and are not to be taken as limiting thereof.

EXAMPLES

Example 1

In Vitro Stimulation of Ciliary Beat Frequency $10^{-4}$ M UTP was applied to isolated airway epithelial cells from normal subjects. Within four minutes, ciliary beat frequency (CBF) increased by $76 \pm 17\%$ as compared to baseline (from $9.3 \pm 0.23$ to $16.12 \pm 0.92$ Hz, n=7, p<0.0001). Similar results were obtained when $10^{+-}$ M UTP was applied to isolated airway epithelial cells from patients afflicted with cystic fibrosis. CBF increased by $56 \pm 17\%$ as compared to baseline (from $11.25 \pm 0.56$ Hz to $16.1 \pm 1.45$ Hz).

Example 2

Treatment of Primary Ciliary Dyskinesia

Uridine 5'-triphosphate (UTP) was administered to patients diagnosed with primary ciliary dyskinesia (PCD) (verified by electron microscopy analysis of ciliary ultrastructure defect from nasal biopsy). The efficacy of UTP was determined by measuring the clearance of an inhaled radiolabeled particle from the lung by radionuclide scanning techniques using a gamma camera. Each subject inhaled an aerosol of iron oxide labeled with Technetium 99m ($^{99}$Tc—$Fe_2O_3$). Subjects inhaled the aerosol for approximately 5 minutes. Subjects were then seated in front of a gamma camera, and for the next 20 minutes subjects randomly inhaled either a saline control (0.12% saline), or $10^{-2}$ M UTP for approximately 20 minutes. After this inhalation, subjects remained seated in front of the gamma camera for the next 30 minutes to measure clearance of the radiolabeled iron oxide. The efficacy of aerosolized UTP in treating primary ciliary dyskinesia was demonstrated by an improvement in cough clearance of Technetium 99m as compared to the saline vehicle alone.

In the same study, the amount of sputum induced by the inhalation of UTP versus placebo was measured. Subjects inhaled either placebo or UTP for 20 minutes according to the method above. For the next 30 minutes, subjects performed 60–90 controlled coughs, and matched sputum samples were collected from 8 of the 12 patients. Total volume of sputum was measured.

Safety data was collected by monitoring heart rate, ECG rhythm strip-Lead II, blood pressure, oxyhemoglobin saturation by pulse oximetry prior to, during, and after inhalation for all dosing periods. All patients during all phases of the study were monitored for any adverse reactions during each dosing period, beginning with inhalation of study drug and ending after the 30-minute scan at 24 hours.

Figure 1:
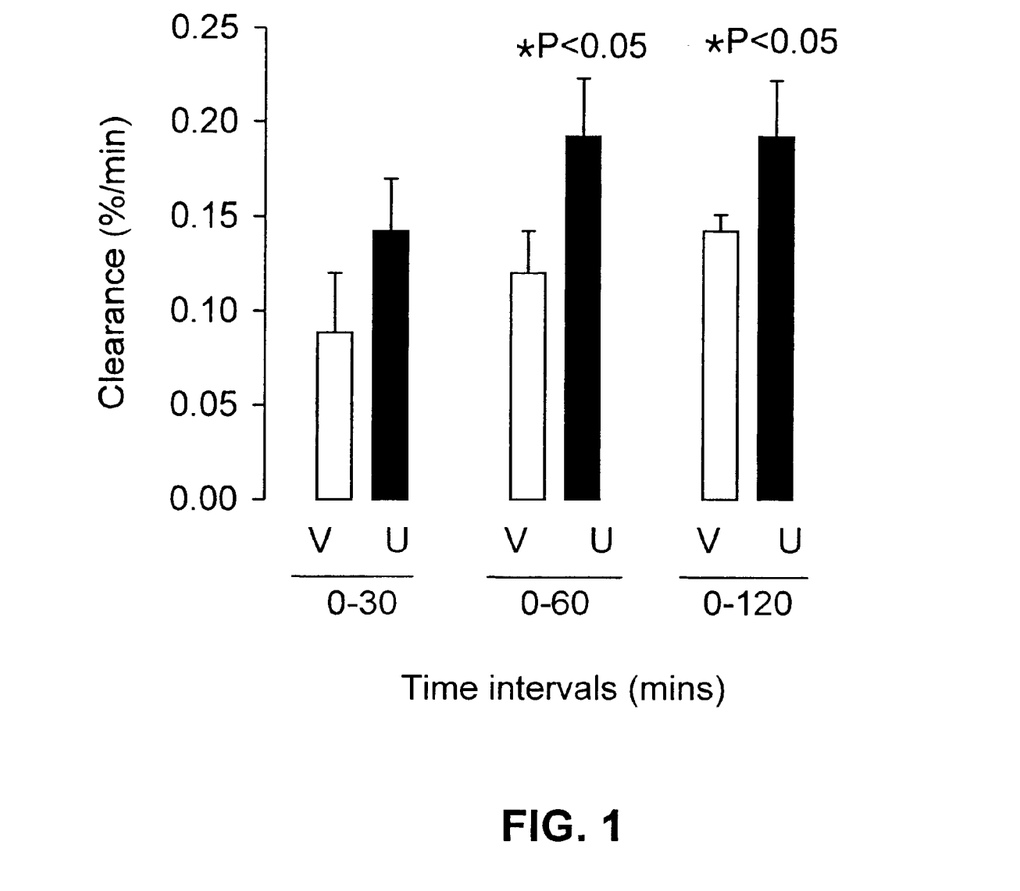
FIG. 1 shows cough clearance from whole lung in PCD patients: Vehicle (V) vs UTP (U).

This was a randomized, double-blind, placebo-controlled, crossover study in 12 patients with PCD, ages 10 and above. FIG. 1 above summarizes data demonstrating that UTP significantly enhanced cough clearance at the 60-minute ($p<0.05$) and 120-minute ($p<0.05$) time points, as compared to placebo (vehicle=V); this improvement also approaches significance at the 30-minute time point. These data are particularly compelling, given that the effect was observed following only a single dose of UTP.

Figure 2:
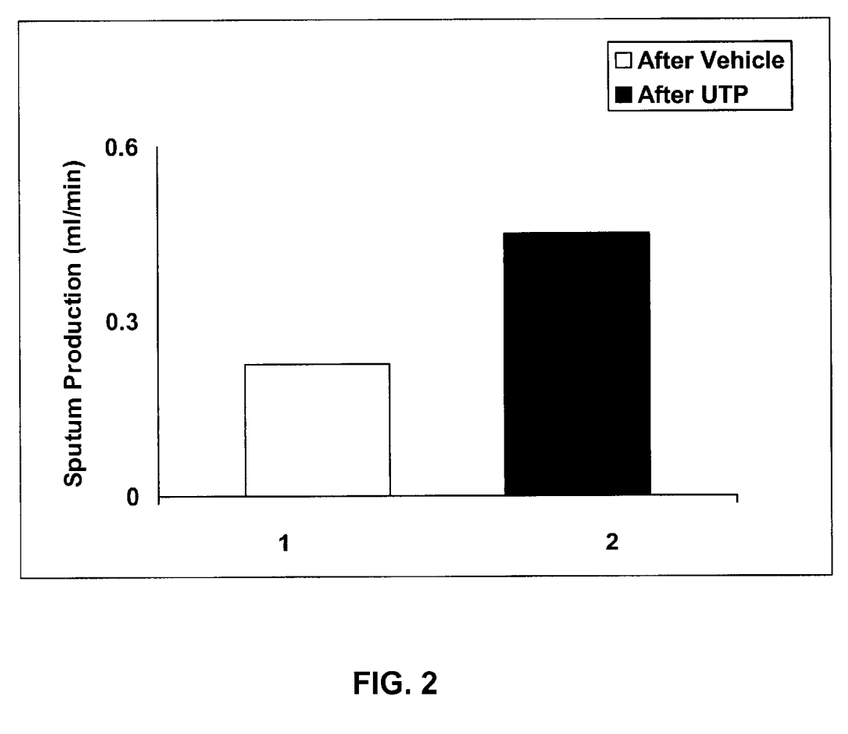
FIG. 2 shows volume of sputum produced per unit time in PCD patients: after vehicle and after UTP administration.

FIG. 2 summarizes data demonstrating that the volume of sputum produced per unit time is also enhanced in PCD patients by the inhalation of UTP. The study was a blinded cross-over design and involved 8 patients. Column 1 shows that approximately 0.2 ml of sputum were expectorated per minute following inhalation of saline vehicle. In contrast, Column 2 shows that inhalation of UTP approximately doubled the amount of sputum expectorated in the same time period ($p<0.01$). Based on data from patient-completed questionnaires (completed in a blinded fashion), UTP appeared to enhance the ease of expectoration relative to vehicle. Several patients stated that sputum was thinner and easier to expectorate following UTP than following vehicle. These data are particularly compelling given that the effect was observed following only a single dose of UTP. The data in FIGS. 1 and 2 indicate that there is a strong correlation between measures of cough clearance and sputum expectoration.

Other embodiments will be evident to those of skill in the art, although the invention has been shown and described with respect to an illustrative embodiment thereof, it should be appreciated that the foregoing and various other changes, omissions, and additions in the form and detail thereof may be made without departing from the scope of the invention as delineated in the claims.

What is claimed is:

1. A method of treating primary ciliary dyskinesia in a subject in need of such treatment, said method comprising:

administering to a subject a pharmaceutical composition comprising a compound of Formula I or IV, or pharmaceutically acceptable salt thereof, in an amount effective to increase ciliary beat frequency in an affected part of the body selected from the group consisting of the lungs, upper airways, eyes, genito-urinary tract, spermatozoa, ovaries, fallopian tubes, neutrophils, and macrophages:

Formula I wherein:
X$_1$, X$_2$, and X$_3$ are each independently selected from the group consisting of OH and SH;
R$_1$ is selected from the group consisting of O, imido, methylene, and dihalomethylene; and wherein Formula I is not uridine triphosphate (UTP); and
R$_2$ is selected from the group consisting of H and Br;

Formula IV wherein:
X is oxygen, methylene, difluoromethylene, imido;
n=0, 1 or 2;
m=0, 1 or 2;
n+m=0, 1, 2, 3 or 4;
Z=OH or N$_3$;
Z'=OH or N$_3$;
Y=H or OH;
Y'=H or OH;
B and B' are each independently a pyrimidine residue as in Formula IVb linked through the 1-position, Formula IVb wherein:
R$_4$ is hydrogen, hydroxy, mercapto, amino, cyano, aralkoxy, C$_{1-6}$ alkylthio, C$_{1-6}$ alkoxy, C$_{1-6}$ alkylamino or dialkylamino, the alkyl groups optionally linked to form a heterocycle;
R$_5$ is hydrogen, acyl, C$_{1-6}$ alkyl, aroyl, optionally functionalized as defined below, C$_{1-5}$ alkanoyl, benzoyl, or sulphonate;
R$_6$ is hydroxy, mercapto, alkoxy, aralkoxy, C$_{1-6}$alkylthio, amino, C$_{1-5}$ disubstituted amino, triazolyl, alkylamino or dialkylamino, where the alkyl groups are optionally linked to form a heterocycle or link to N$^3$ to form an optionally substituted ring; or R$_5$ and R$_6$ taken together form a 5-membered fused imidazole ring between positions 3 and 4 of the pyrimidine ring optionally substituted on the 4- or 5-positions of the etheno moiety with alkyl, aryl or aralkyl moieties as defined below;
R$_7$ is hydrogen, hydroxy, cyano, nitro, alkenyl with the alkenyl moiety optionally linked through oxygen to form a ring optionally substituted on the carbon adjacent to the oxygen with alkyl or aryl groups, substituted alkynyl, halogen, substituted alkyl, perhalomethyl, C$_{2-6}$ alkyl, C$_{2-3}$ alkenyl, or substituted ethenyl, C$_{2-3}$ alkynyl or substituted alkynyl; or together R$_6$–R$_7$ may form a 5 or 6-membered saturated or unsaturated ring bonded through N or O at R$_6$, such a ring may contain substituents that themselves contain functionalities;
provided that when R$_8$ is amino or substituted amino, R$_7$ is hydrogen; and
R$_8$ is hydrogen, amino or substituted amino, alkoxy, arylalkoxy, alkylthio, arylalkylthio, carboxamidomethyl, carboxymethyl, methoxy, methylthio, phenoxy or phenylthio; or
pharmaceutically acceptable esters, amides or salts thereof.

2. The method according to claim 1, wherein said compound is delivered to the eyes to treat dysfunction of the ocular mucociliary clearance system as a result of impaired ciliary movement in a patient in need of such treatment.

3. The method according to claim 1, wherein said compound is delivered to the genito-urinary tract to treat dysfunction of the genito-urinary mucociliary clearance system as a result of impaired ciliary movement in a patient in need of such treatment.

4. The method according to claim 1, wherein said compound is delivered to the bloodstream to treat immune deficiency caused by impairment of ciliary movement of neutrophils and macrophages in a patient in need of such treatment.

5. The method according to claim 1, wherein said compound is delivered to the spermatozoa to treat male infertility caused by impairment of ciliary movement of spermatozoa in a patient in need of such treatment.

6. The method according to claim 1, wherein said compound is delivered to the ovaries or fallopian tubes to treat female infertility caused by impairment of ciliary movement of the epithelial cells of the ovaries or fallopian tubes in a patient in need of such treatment.

7. The method according to claim 1, wherein said compound is delivered by administering a liquid, a liquid suspension, or an aerosal suspension of said compound to the nasopharyngeal airways or oral airways of said subject, such that a therapeutically effective amount of said compound contacts the area of impaired ciliary movement in the lungs, sinuses, middle ear, inner ear, upper airways, eyes, genito-urinary tract, spermatozoa, ovaries, fallopian tubes, neutrophils, or macrophages of said subject either directly or via systemic absorption and circulation.

8. The method according to claim 1, wherein said compound is delivered by administering an oral form of said compound to said subject, such that a therapeutically effective amount of said compound contacts the area of impaired ciliary movement in the lungs, sinuses, upper airways, middle or inner ear, eyes, genito-urinary tract, spermatozoa, ovaries and fallopian tubes, or neutrophils and macrophages of said subject either directly or via systemic absorption and circulation.

9. The method according to claim 1, wherein said compound is delivered by administering a topical form, an injected form, or a suppository form of said compound to the middle ear or eyes via the tympanic membrane or cornea of said subject, such that a therapeutically effective amount of said compound contacts the area of impaired ciliary movement in the luminal epithelial lining of the middle ear or inner ear or the lens of said subject.

10. The method according to claim 1, wherein said compound is delivered by intra-operative instillation of a gel, cream, or liquid suspension form of said compound, such that a therapeutically effective amount of said compound contacts the area of impaired ciliary movement in the ears, eyes, lungs, upper airways or genito-urinary tract of said subject either directly or via systemic absorption and circulation.

11. The method according to claim 1, wherein said compound is administered ex vivo to the spermatozoa by means of a topical, injection, or immersion form of the compound, such that a therapeutically effective amount of said compound contacts the spermatozoa having impaired ciliary movement.

12. The method according to claim 1, wherein said compound is delivered via a transdermal patch, such that a therapeutically effective amount of said compound contacts the area of impaired ciliary movement in the ears, eyes, lungs, upper airways or genito-urinary tract of said subject either directly via local absorption or via systemic absorption and circulation.

13. The method according to claim 1, wherein said compound is delivered to the affected part of the body to treat inflammation caused by viral or bacterial infection.

14. The method according to claim 1, wherein said compound is delivered to upper airways to treat upper respiratory infection.

15. The method according to claim 1, wherein said compound is administered in an amount sufficient to achieve concentrations thereof on the surfaces of the lungs, sinuses, middle or inner ear, upper airways, eyes, genito-urinary tract, spermatozoa, ovaries or fallopian tubes, or neutrophils and macrophages of said subject of from about $10^{-7}$ to about $10^{-1}$ moles/liter.

* * * * *